US011969460B2

(12) United States Patent
Butler et al.

(10) Patent No.: US 11,969,460 B2
(45) Date of Patent: Apr. 30, 2024

(54) METHODS AND COMPOSITIONS FOR TREATING DECREASED COGNITIVE ABILITY

(71) Applicants: Saint Louis University, St. Louis, MO (US); U.S. DEPARTMENT OF VETERANS' AFFAIRS, Washington, DC (US)

(72) Inventors: Andrew Alistair Butler, St. Louis, MO (US); Susan Farr, St. Louis, MO (US); Clemence Girardet, Paris (FR)

(73) Assignees: Saint Louis University, St. Louis, MO (US); U.S. Department of Veternas Affairs, Washington, DC (US)

( * ) Notice: Subject to any disclaimer, the term of this patent is extended or adjusted under 35 U.S.C. 154(b) by 0 days.

(21) Appl. No.: 17/054,740

(22) PCT Filed: Jun. 4, 2019

(86) PCT No.: PCT/US2019/035428
§ 371 (c)(1),
(2) Date: Nov. 11, 2020

(87) PCT Pub. No.: WO2019/236603
PCT Pub. Date: Dec. 12, 2019

(65) Prior Publication Data
US 2021/0252108 A1 Aug. 19, 2021

Related U.S. Application Data

(60) Provisional application No. 62/682,717, filed on Jun. 8, 2018.

(51) Int. Cl.
*A61K 38/22* (2006.01)
*A61P 25/28* (2006.01)
*A61K 48/00* (2006.01)

(52) U.S. Cl.
CPC .............. *A61K 38/22* (2013.01); *A61P 25/28* (2018.01); *A61K 48/00* (2013.01)

(58) Field of Classification Search
None
See application file for complete search history.

(56) References Cited

U.S. PATENT DOCUMENTS

| | | | | |
|---|---|---|---|---|
| 8,518,892 B2 * | 8/2013 | Butler | ................ | C07K 14/47 514/21.3 |
| 9,458,209 B2 | 10/2016 | Novartis | | |
| 2003/0096951 A1 * | 5/2003 | Jacobs | ................ | C07K 16/18 530/350 |
| 2010/0306866 A1 | 12/2010 | Butler et al. | | |
| 2013/0085105 A1 * | 4/2013 | Deasy | ................ | A61K 9/0014 514/11.1 |
| 2021/0252108 A1 * | 8/2021 | Butler | ................ | A61P 3/04 |

OTHER PUBLICATIONS

Kumar et al. Identification of Adropinasa Secreted Factor linking Dietary Macronutrient Intake with Energy Homeostasis and Lipid Metabolism. Cell Metabolism. Dec. 2008. vol. 8, No. 6: pp. 468-481.*

Sato et al. Adropin Contributes to Anti-Atherosclerosis by Suppressing Monocyte-Endothelial Cell Adhesion and Smooth Muscle Cell Proliferation. Int. J. Mol. Sci. 2018, 19(5), 1293; https://doi.org/10.3390/ijms19051293 and https://www.mdpi.com/1422-0067/19/5/1293.*

Ghoshal et al. Adropin: An endocrine link between the biological clock and cholesterol homeostasis. Molecular Metabolism. vol. 8, Feb. 2018, pp. 51-64. https://www.sciencedirect.com/science/article/pii/S2212877817307585?via%3Dihub.*

Yu et al. Serum adropin levels are decreased in patients with acute myocardial infarction. Regulatory Peptides vols. 190-191, May 2014, pp. 46-49. https://www.sciencedirect.com/science/article/pii/S0167011514000275.*

Goetze et al. Adropin: A new regulatory peptide in cardiovascular endocrinology. Regulatory Peptides vols. 190-191, May 2014, pp. 41-42. https://www.sciencedirect.com/science/article/pii/S0167011514000287.*

Altintas et al. Neuroprotective effect of ischemic preconditioning via modulating the expression of adropin and oxidative markers against transient cerebral ischemia in diabetic rats. Peptides vol. 79, May 2016, pp. 31-38. https://www.sciencedirect.com/science/article/pii/S0196978116300468.*

Aydin et al. Elevated adropin: a candidate diagnostic marker for myocardial infarction in conjunction with troponin-l. Peptides, 58 (2014), pp. 91-97. https://www.sciencedirect.com/science/article/pii/S0196978114001740.*

Celik et al. Deficiency of a new protein associated with cardiac syndrome X; called adropin. Cardiovasc. Ther., 31 (3) (2013), pp. 174-178. https://onlinelibrary.wiley.com/doi/10.1111/1755-5922.12025.*

Lian et al. Elevated plasma levels of adropin in heart failure patients. Intern Med, 50 (2011), pp. 1523-1527. https://www.jstage.jst.go.jp/article/internalmedicine/50/15/50_15_1523/_article.*

Wu et al. Low serum adropin is associated with coronary atherosclerosis in type 2 diabetic and non-diabetic patients Clin Chem Lab Med, 52 (2014), pp. 751-758. https://www.scopus.com/record/display.uri?eid=2-s2.0-84898941309&origin=inward&txGid=824aa9378d8a3d818e481225080ad28b.*

Lovren et al. Adropin is a novel regulator of endothelial function. Circulation, 122 (2010), pp. S185-S192. https://www.ahajournals.org/doi/10.1161/CIRCULATIONAHA.109.931782.*

(Continued)

*Primary Examiner* — Maury A Audet
(74) *Attorney, Agent, or Firm* — Randolph Bretton; The Law Office of Randolph Bretton

(57) ABSTRACT

Disclosed are methods and compositions for treating cognitive decline in subjects in need. More specifically, disclosed are methods of administrating exogenous adropin to subjects suffering from, or at risk of, cognitive decline. Also disclosed are subjects who would benefit from such treatment and pharmaceutical acceptable compositions comprising adropin, adropin$^{34-76}$, and derivatives or variations thereof.

11 Claims, 15 Drawing Sheets

Specification includes a Sequence Listing.

(56) References Cited

OTHER PUBLICATIONS

Kumar et al. Identification of adropin as a secreted factor linking dietary macronutrient intake with energy homeostasis and lipid metabolism. Cell Metab, 8 (2008), pp. 468-481. https://www.sciencedirect.com/science/article/pii/S1550413108003525.*

Butler et al. Low circulating adropin concentrations with obesity and aging correlate with risk factors for metabolic disease and increase after gastric bypass surgery in humans. J Clin Endocrinol Metab, 97 (2012), pp. 3783-3791. https://www.sciencedirect.com/science/article/pii/S0167011514000275.*

Kumar. KG et al., Identification of Adropin as a Secreted Factor linking Dietary Macronutrient Intake with Energy Homeostasis and Lipid Metabolism. Cell Metabolism. Dec. 2008. vol. 8, No. 6: pp. 468•481: abstract; p. 7, 3rd paragraph: 001: 10.1016fj.cmel.2008.10.011.

Yang, C et al. Age•Dependent Decrease in Adropin is Associated with Reduced Levels of Endothelial Nitric Oxide Synthase and Increased Oxidative Stress in the Rat Brain. Aging and Disease. Apr. 2018, vol. 9. No. 2: pp. 322-330; 001: 10.14336'AD.2017.0523.

Ghoshal. S et al., Adropin: An endocrine link between the biological clock and cholesterol homeostasis. Molecular Metabolism. Feb. 2019. Epub Dec. 30, 2017, vol. 8: pp. 51-64: 001: 10.1016fj.molmel.2017.12.002.

International Searching Authority, Notification of Transmittal of ISR and Written Opinion, Nov. 5, 2019.

Yang, C et al. Adropin is Profoundly Neuroprotective in Experimental Ischemic Stroke, Feb. 2017, vol. 48, Issue Suppl 1(Abstract).

Pepeu (2004) Mild cognitive impairment: animal models, Dialogues in Clinical Neuroscience, 6:4, 369-377.

Analyzing JAX Aged C57BL/6J mice for NASH phenotypes, Jax labs, TS002.

American Academy of Neurology: Practice Guideline Update: Mild Cognitive Impairment (2017).

* cited by examiner

METHODS AND COMPOSITIONS FOR TREATING DECREASED COGNITIVE ABILITY

CROSS REFERENCE TO RELATED APPLICATIONS

This application claims priority to U.S. provisional application 62/682,717, filed Jun. 8, 2018, hereby incorporated by reference in its entirety.

GOVERNMENT SUPPORT CLAUSE

The work disclosed herein was supported by award no. R21NS108138. The U.S. Government has certain rights in this invention.

FIELD OF THE INVENTION

The invention relates to methods and compositions for treating reduced cognitive ability. More specifically, the invention relates to using the polypeptide adropin to treat subjects with decreased cognitive ability, including decreased cognitive ability due to age related dementia.

BACKGROUND

'Dementia' as a general term describes memory loss and other cognitive deficits severe enough to make normal daily life difficult or impossible. Neurodegenerative conditions such as Alzheimer's disease (AD), Parkinson's disease and the degenerative dementias (Lewy body, Frontotemporal) represent a pressing health problem for industrialized nations. 'Mild Cognitive Impairment' describes an intermediate stage between cognitive decline that is expected with aging, and the more serious declines observed in dementia. The incidence of these conditions is predicted to increase owing to an aging populace. By 2030, 1 in 5 Americans will be aged 65 years or older. Metabolic disease may also be a predisposing risk factor for neurodegenerative conditions. Type 2 diabetes is a predisposing risk factor for cognitive decline and dementia. Cardiovascular disease, obesity and insulin resistance are also associated with increased risk for neurocognitive decline. The number of people considered obese or overweight now outnumbers those considered to have a healthy body mass index by 2 to 1. The conditions are thus being established for a dramatic rise in the incidence of debilitating neurodegenerative disorders. An increased occurrence of dementias in an aging and increasingly obese population thus represents a clear challenge to the US economy and the health care system. In the absence of new clinical interventions to treat cognitive decline, more than 12 million Americans may suffer from neurodegenerative diseases within 30 years. The search for treatments that delay or prevent cognitive decline is thus an imperative.

Unfortunately, few options are currently available for treating dementias. Health and longevity are maintained, at least in part, by secreted peptides signaling metabolic condition at a cellular and organismal level. The secreted peptide adropin was identified by one of the inventors as such a signal. The involvement of adropin in metabolic control, was documented, showing that the putative secreted domain (adropin$^{34-76}$) rapidly alters activity of intracellular signaling molecules (e.g., SIRT1, Pgc1α) regulating glucose and fatty acid metabolism. While adropin is most abundant in the central nervous system, its functions as a neuropeptide remain unknown. The Inventors have made the surprising discovery that the decline in cognitive performance associated with aged subjects may be slowed, delayed, or prevented by sustained adropin activity in the brain.

SUMMARY OF THE INVENTION

A method of treating cognitive decline in a subject in need, the method comprising administering an effective amount of Adropin, Adropin$^{34-76}$, or variants or derivatives thereof, to the subject parenterally.

A method of treating cognitive decline, whereby the effective amount of Adropin, Adropin$^{34-76}$, is 1000 nmol/kg/day to about 1 nmol/kg/day, preferably about 450 nmol/kg or most preferably about 90 nmol/kg/day.

A method of treating cognitive decline, in a subject wherein the subject is a human subject.

A method of treating cognitive decline, in a subject at risk, including subjects diagnosed with mild cognitive impairment, dementia, hypercholesterolemia, type 2 diabetes, a metabolic dysregulation disorder or advanced age.

A method of treating cognitive decline, wherein the effective amount is administered one or more times a day, over a period of 2 weeks or over the remaining life of the subject.

A method of treating cognitive decline, wherein administering an effective amount consists of administrating an oligonucleotide enabled to express an effective amount of Adropin or Adropin$^{34-76}$.

A method of treating cognitive decline, wherein administering an effective amount includes intraperitoneal, subcutaneous, intramuscular, or intravenous injection.

A composition for treating age related dementia, comprising Adropin, Adropin$^{34-76}$, or variants or derivatives thereof, prepared in a pharmaceutically acceptable aqueous solution.

A composition for treating age related dementia, comprising Adropin, Adropin$^{34-76}$, or variants or derivatives thereof, prepared in a pharmaceutically acceptable aqueous solution further including but not limited to one or more pharmaceutically acceptable salts, proteins, polypeptides, and preservatives glycerol, liquid polyethylene glycol, and pharmaceutically acceptable oils, A composition for treating age related dementia, comprising Adropin, Adropin$^{34-76}$, or variants or derivatives thereof, prepared in a dehydrated or concentrated form, for later use after hydration.

A composition for treating age related dementia, comprising Adropin, Adropin$^{34-76}$, prepared in pharmaceutically acceptable aqueous solution, whereby the composition is not found in nature.

REFERENCE TO COLOR FIGURES

The application file contains at least one figure executed in color. Copies of this patent application publication with color photographs will be provided by the Office upon request and payment of the necessary fee.

DETAILED DESCRIPTION OF THE INVENTION

Figure 1:
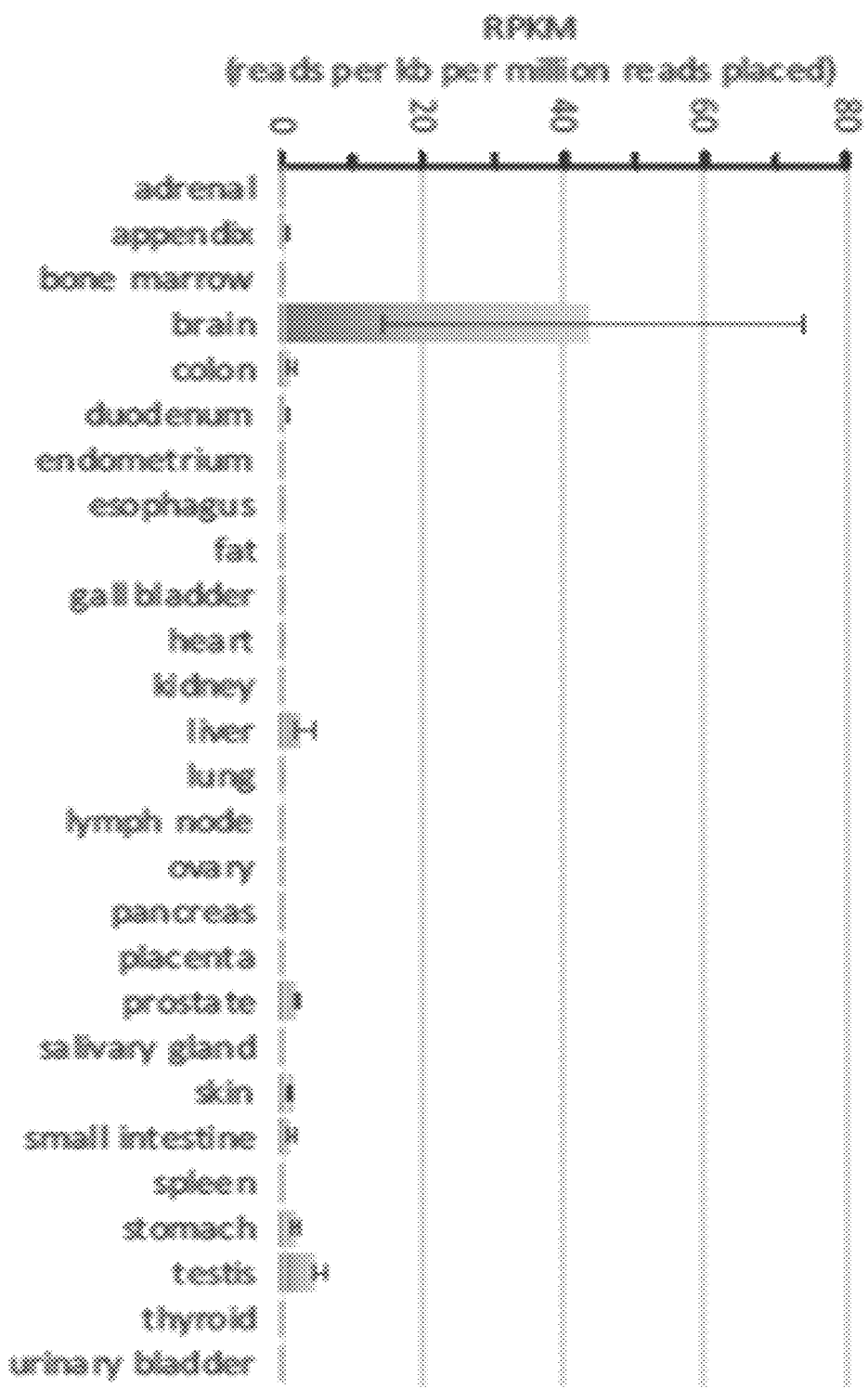
FIG. 1 Illustrates the relative expression of the ENHO transcript in human tissues (adapted from Mol Cell Proteomics. 2014 Feb. 13(2):397-406).
Figure 3:
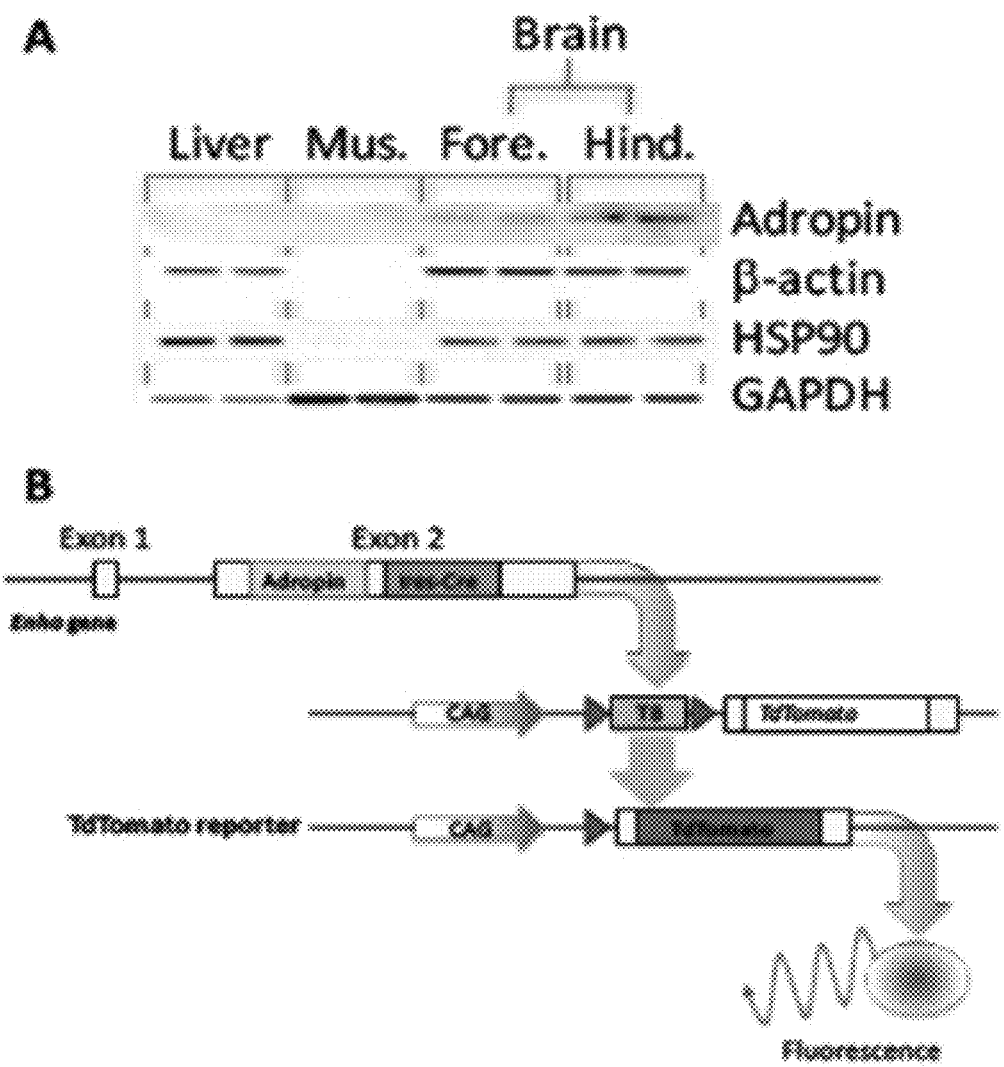
FIG. 3 Illustrates (A) Analysis of adropin protein in tissues by western blot. Tissues were homogenized in RIPA buffer; 50 μg of total protein was used in the blot. (B) Schematic of the B6.Enho-Cre mouse. An IRES ("internal ribosomal entry site")-Cre inserted in the 3' UTR of the Enho gene of C57BL/6J (B6) mice drives Cre-mediated recombination of genomic DNA flanked by LoxP sites. B6.Enho-Cre mice were crossed with B6.Cg-Gt(ROSA)26 Sor$^{tm9(CAG-tdTomato)Hze}$/J (tdTomato) mice. Enho(+ve) cells are identified by activation of tdTomato expression, resulting from Cre-mediated removal of a transcriptional block (TB) 5' of the tdTomato open reading frame; the tdTomato can be visualized directly when exposed to yellow-green light or by immunohistochemistry (IHC).

Neurodegenerative diseases are a pressing health problem for industrialized nations for which few treatments are currently available. Health and longevity are maintained, at least in part, by secreted peptides signaling metabolic condition at an organismal and cellular level. One of the Inventors identified the secreted peptide adropin as such a signal in 2008. Full length adropin protein (76 aa) is encoded by the Energy Homeostasis Associated (ENHO) gene which is located on human chromosome 9p13.3. Adropin is a secretory signal peptide. Early analyses of adropin function suggested links with insulin resistance and the control of carbohydrate and lipid metabolism in the periphery. Recent studies suggest a protective role in cerebral ischemia. (Yang et al. (2018) *Aging and Disease.;* 9 (2): 322-330). The Inventors have reported associations between plasma adropin concentrations and relative intake of fats and carbohydrates, and further demonstrated a metabolic response to exogenously administered adropin$^{34-76}$, when they delivered the putative secretory domain (adropin$^{34-76}$) to mice by intraperitoneal injection. (Stevens, et al., (2016) *Obesity* 24, 1731-1740; St-Onge, et al., (2014) *Obesity* 22, 1056-1063). Initial examination of ENHO expression using northern blot suggested abundant expression in mouse brain and liver (Kumar, et al., (2008) *Cell metabolism,* 8, 468-481), whereas recent studies using RNA-seq in humans suggest adropin expression is most abundant in brain (FIG. 1). An independent lab reported adropin protein in mice is most abundant in the CNS. (Wong, et al., (2014) *The Journal of biological chemistry* 289, 25976-25986). The Inventors' analysis using a monoclonal antibody confirms abundant adropin immunoreactivity in the CNS relative to peripheral tissues of male C57BL/6J (B6) mice FIG. 3A). Adropin may function primarily as a neuropeptide, with circulating adropin originating predominately from the CNS.

Figure 2:
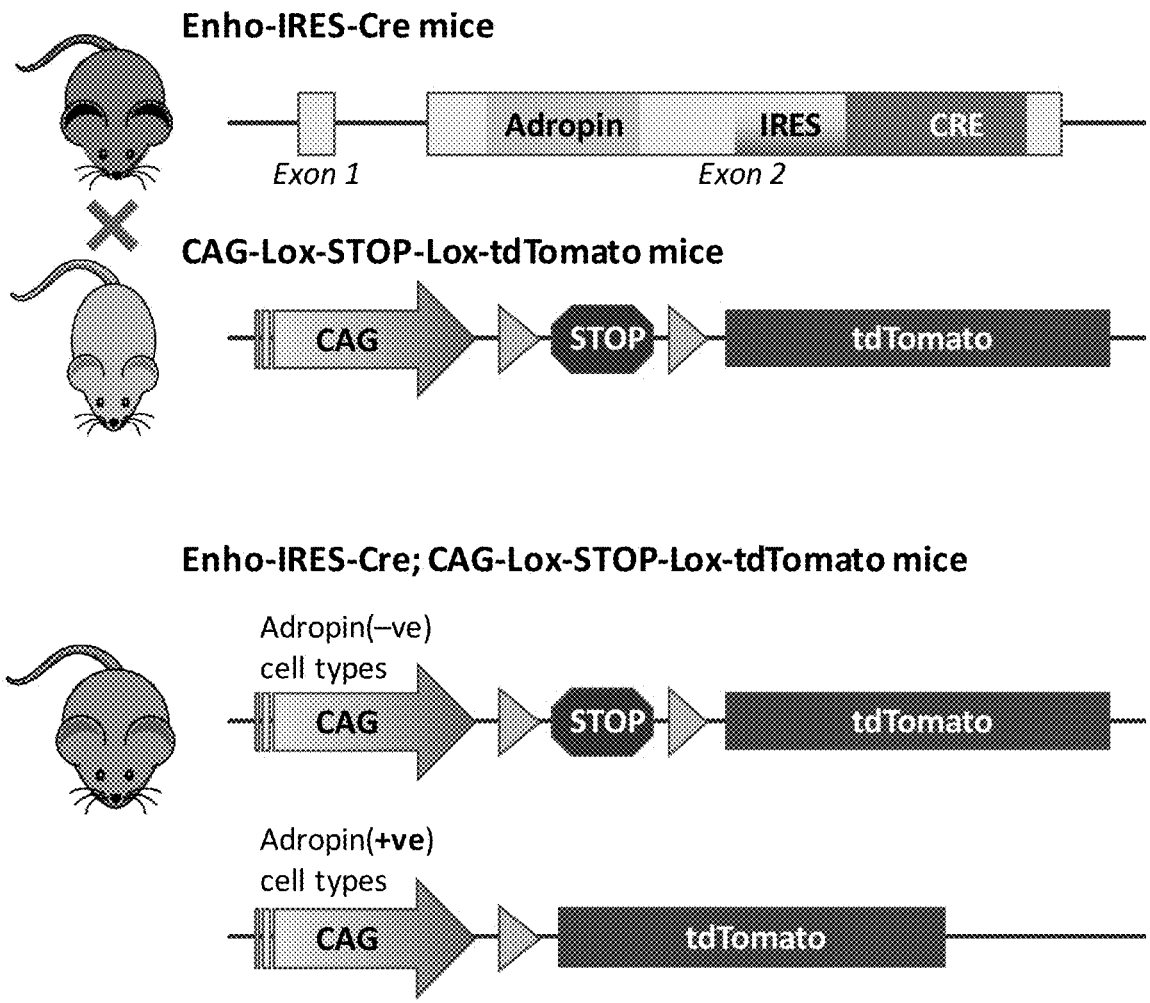
FIG. 2 Illustrates the modification of the mouse Enho gene with the internal ribosomal entry site (IRES) and causes-recombination (Cre) coding sequence inserted into the 3'-UTR in exon 2. B6.Enho-Cre mice were mated with B6.Cg-Gt(ROSA)26Sor$^{tm9(CAG-tdTomato)Hze}$/J (Ai9) strain that have a loxP-flanked STOP cassette that prevents transcription of a CAG-promoter-driven variant of the red fluorescent protein (tdTomato). In cells expressing the Enho transcript, expression of Cre results in removal of the STOP cassette by site-specific recombination.
Figure 4:
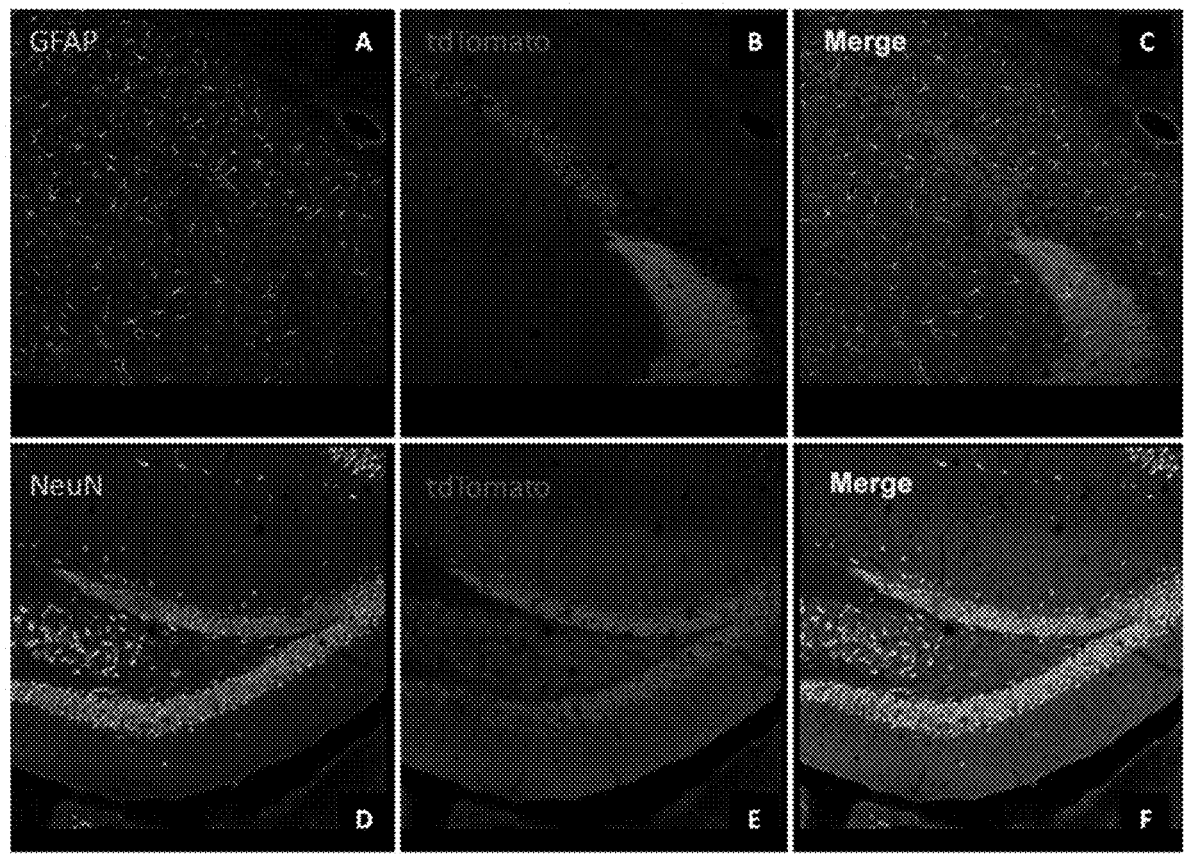
FIG. 4 representative photomicrographs showing tdTomato expression in the hippocampus (A-D). Enho-Cre mice crossed with Ai9 reporter strain allow visualization of adropin expressing cells in the hippocampus. (A-C) Codetection of GFAP (A) and tdTomato (B). The merged image (C) suggests that hippocampal astrocytes are devoid of adropin; (D-F) Codetection of NeuN with tdTomato.

Analysis of Enho expression in the mouse brain using in situ hybridization in one of the inventor's laboratories, initially indicated a very broad distribution but were unable to define the cell-types and areas of expression (Kumar, et al., (2008) *Cell metabolism,* 8, 468-481). The Inventors were able to show, using a Cre-inducible reporter mouse, that adropin is expressed in hippocampal neurons. To identify cell-types expressing adropin, the "ENHO-Cre" strain was developed (FIG. 2). Mating ENHO-Cre mice with the tdTomato reporter strain (Madisen, et al, (2010) *Nature Neuroscience* 13, 133-140) allows for visualizing cell-types expressing adropin, mediated by Cre-removal of a LoxP-flanked transcription block (TB) (FIG. 2B, C). These studies indicate hippocampal pyramidal neurons express adropin (FIG. 4), suggesting a potential role in cognition.

Analysis of mRNA expression indicates that adropin is most abundant in the CNS (Kumar et al., (2008) Cell metabolism 8(6):468-81; Wong et al., (2014) *The Journal of biological chemistry* 289(37):25976-86). Immunohistochemistry also indicates high expression of adropin in the CNS (FIG. 3A).

The inventors have engineered transgenic mice that over express adropin ("AdrTG") in the nervous system and peripheral tissues. They found that continuous elevated adropin in the CNS protects cognitive function during aging. In addition, reduced JNK phosphorylation and expression of cytokines indicates reduced neuroinflammatory processes. Inflammation is also increasingly considered an important predisposing risk factor for age-related neurodegeneration (Irwin & Vitiello (2019) Lancet Neurol. 18(3):296-306; Madhavan et a., Nat Rev Cardiol. 15(12):744-756). The transgenic mice demonstrate a delay or prevention in the decline of learning and memory associated with aging. The inventors demonstrated improved cognition in older subjects with continuous elevated adropin compared to age-matched controls, through the use of cognitive assessments: novel object recognition; spatial memory acquisition; and retention, using an aversive T-maze. When the inventors compared C57BL/6J adropin transgenic mice (AdrTG) with littermate controls, they found that while cognitive performance is normal in young (less than 12 month) AdrTG, mice, old (18 month) AdrTG mice exhibit significantly better memory acquisition and retention compared to age-matched controls. In addition, the inventors have also shown that adropin levels may be increased systemically by endogenous administration. When adropin was administered via intraperitoneal injection, the subjects with diet-induced obesity experienced metabolic changes suggesting improvements in glucose control and reduced risk for type 2 diabetes. (Kumar et al. 2008; Gao et al. 2014, 2015)

The Inventors disclose a method of treating cognitive declines in aged subjects by increasing levels of adropin in the subject's brain by way of exogenous administration.

In one embodiment, subjects experiencing or at risk of age-related dementia are treated by intravenous, subcutaneous, or intraperitoneal injection of adropin, adropin$^{34-76}$, or variants or derivatives thereof.

In another embodiment, is an injectable preparation of adropin, adropin$^{34-76}$, or variants or derivatives thereof, and a pharmaceutical acceptable preparation. A pharmaceutical acceptable preparation may also include a preservative, a composition to block non-specific binding of adropin, by way of example a protein such as gelatin or albumin, or a compound, such as a surfactant, by way of example, Tween 20 preferably at 0.1 to 1 percent. The solution may also include compounds to prevent degradation or aggregation of the peptide while staying within physiological acceptable parameters for injection. By way example, the pH may vary from 5.0 to 6.0, 6.0 to 7.0, 7.0, to 8.0, or 9.0 to 10.0. One or more salts may also be included. By way of non-limiting example, a phycological acceptable concentration of salt may be a concentration, plus or minus up to 5, 10, or 15 percent that normally found in the subject. Non-naturally occurring salts may also be included, by way of example, Tris, HCL. Formulations of adropin may be concentrated to some degree or lyophilized for storage and later hydrated before use.

The aqueous solution may further contain various salts or buffers that are well known in the art. Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are, Ringer's solution, or isotonic sodium chloride solution.

Adropin Sequences
Human adropin Amino Acid Sequence (SEQ ID NO.:1):

```
          10         20         30         40
  MGAAISQGAL IAIVCNGLVG FLLLLLWVIL CWACHSRSAD
          50         60         70
  VDSLSESSPN SSPGPCPEKA PPPQKPSHEG SYLLQP
```

Adropin$^{34-76}$, peptide used in the examples for inducing metabolic and cognitive activity (SEQ ID NO.:2):

```
34                                                76
CHSRSAD VDSLSESSPN SSPGPCPEKA PPPQKPSHEG SYLLQP
```

The sequences disclosed herein represent non-limiting examples. It is anticipated that variations of Adropin and Adropin$^{34-76}$, may also be effective, particularly those with conservative amino acid substitutions. In addition, variants, analogs and derivatives of Adropin polypeptide sequences are anticipated including but not limited to the following list of possible modifications. Chemical design strategies to avoid aggregation, including corruption of hydrophobic patches by means of amino acid substitutions or N-methylation of amino acids. Physicochemical properties of adropin may be improved by the introduction of stabilizing α-helixes, introduction of salt bridge formations or lactam bridges. The half-life may be extended through identifying cleavage sites and substitution of amino acids, stabilizing the secondary structure of the molecule, peptide acylation, insertion of albumin-binding elements into the peptides backbone, conjunction to antibody fragments, or polyethylene-glycol (PEG)-ylation.

Sequence identity or percent identity is intended to mean the percentage of same residues between two sequences. In sequence comparisons, the two sequences being compared are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NBRF, Washington, Vol. 5, suppl. 3, p. 345, 1978).

Variations in the amino acid sequence will likely be comprised of conservative amino acid substitutions, or substitutions of amino acids outside of function regions. It is anticipated that polypeptides with 85 percent or more, 90 percent or more, 95 percent or more or 98 percent of more identity to Adropin and Adropin$^{34-76}$, may be effective at treating cognitive decline. It is also anticipated that the variants described herein include variants not found in nature.

Subjects

It is envisioned that subjects selected for treatment would include human subjects, particularly human subjects diagnosed with dementia, or suffering from cognitive decline or at risk for cognitive decline. Human subjects at risk for cognitive decline, would include, by way of example, the elderly, subjects at risk for, or who have experienced: stroke, Parkinson's Disease, people identified as being "at risk" for early-onset Alzheimer's disease including those with a family history or with risk genes: APOE-e4, amyloid precursor protein, presenilin-1, presenilin-2), traumatic brain injury, chronic poorly-controlled hypertension, type 2 diabetes, sleep apnea, disruption of normal sleeping patterns, elevated biomarkers of systemic and/or cerebral inflammation, hypercholesterolemia, and tests for biomarkers in the blood plasma that are currently under development. Surgical interventions have also been indicated to induce inflammation in the nervous system and dementia. The inventors anticipate administration of endogenous adropin or adropin$^{34-76}$ may be used as an effective post-operative prophylactic to reduce risk for dementia in elderly patients.

Other subjects who may benefit from Adropin treatment include, by way of non-limiting example, laboratory test animals, livestock, show animals and house hold pets.

Treatment

Adropin, Adropin$^{34-76}$, or variants. analogs, or derivates thereof, may be administered to a subject parenterally. By way of non-limiting example, by subcutaneous, intramuscular, intraperitoneal, or intravenous injection. Solutions or suspensions of the peptide may be prepared in pharmaceutically acceptable salts as an aqueous solution. Peptide solutions may also be prepared in glycerol, liquid polyethylene glycols, or mixtures thereof of pharmaceutically acceptable oils. A preservative may be added to the peptide preparation to prevent microbial growth. Preparations may also contain a pharmaceutically acceptable protein, such as gelatin or albumin, to inhibit nonspecific binding of the protein to storage vehicles. By way of example, studies in mice using adropin$^{34-76}$ to improve cognition have used 0.1% bovine serum albumin for this purpose.

Using mice, the Inventors have shown that administration of adropin$^{34-76}$, in doses as low as 90 nmol/kg/day, delivered as two 45 nmol/kg injections, can be effective in producing changes in metabolism. Dose as high as 900 nmol/kg/d are well tolerated in mice. While the doses required for a desired clinical effect in humans is expected to vary between patients, the 90 nmol/kg dose administered by subcutaneous, intramuscular, or intravenous injection, either once or twice a day, may represent a preferred treatment protocol. It is anticipated that the treatments would be administered daily, although long-acting formulations involving weekly injections are envisaged. The optimum dose and frequency for a particular subject may be determined by the patient's treating physician, based on the patient's cognitive response. It is anticipated that adropin therapy may or may not improve a subject's cognitive function relative to current baseline, however adropin therapy may result in significant delays in the advancement of the disease. Improvement may manifest as a significant delay or a reduced rate of subsequent cognitive decline.

In one non-limiting embodiment, is a human subject, exhibiting evidence of age-related cognitive decline or dementia, treated with an injection of about 450 nmol/kg of adropin$^{34-76}$, a dose known to affect metabolic control in male B6 mice. Symptoms of dementia can vary greatly between human subjects. At least two of the following core mental functions must be significantly impaired for a diagnosis of dementia to be considered: memory, communication and language, ability to focus and pay attention, reasoning and judgement, visual perception. Medical doctors will diagnose Alzheimer's and other types of dementia based on a careful examination of medical history; physical examination; laboratory tests; characteristic changes in thinking; and assessment of day-to-day function and behavior associated with each type and can determine that a person has dementia with a high level of certainty. It is more difficult to determine the exact type of dementia because symptoms and changes in brain morphology of the different types of dementias can overlap. In some cases, a doctor may diagnose "dementia" and not specify a type. The term dementia, as used herein, is meant to include all forms of dementia. Non-limiting symptoms of dementia included loss of: memory, communication and language skills, an ability to focus and pay attention, reasoning and judgment, as well as visual perception. It is anticipated that treatment would be initiated soon after the diagnosis of dementia. The treatment will be repeated daily for the remaining life of the subject. Similar subjects may receive sham treatment. After an appropriate period of time for the particular subject, both groups will be subjected to cognitive testing. It is anticipated that subjects receiving adropin or continuous adropin administration, will perform better on cognitive testing compared to subjects receiving sham treatment.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Materials and Methods

Using a Cre-inducible reporter model developed by the Inventors (FIG. 3), adropin expression was observed in hippocampal neurons (FIG. 4) typically related to learning and memory (Eichenbaum et al., (2017) Curr Opin Behav Sci. 2017; 17, 65-70).

The AdrTG model used for these experiments was developed by the Inventors using a human β-actin promotor to drive overexpression of the adropin open reading frame in a synthetic gene in B6 mice (Kumar, et al., (2008) Cell metabolism, 8, 468-481; Gao, et al., (2014) Diabetes 63, 3242-3252). Increased expression of adropin is evident in all tissues examined, including the nervous system (Id.) and data not shown, particularly in tissues where expression of the endogenous gene is low (for e.g., skeletal and cardiac muscle, adipose tissue). An analysis of adropin expression in the hippocampus of male mice housed at SLU suggests a 40% increase in relative expression (WT, 1.00±0.02, n=6; AdrTG, 1.42±0.07, n=7; p<0.01 by Student's t-test).

Transgenic Mouse Model

AdrTG were generated and maintained as previously described (Kumar et al., (2008) Cell metabolism.; 8(6):468-481; Ghoshal et al., (2018) Molecular metabolism 8:51-64; Gao S, et al., (2014) Diabetes. 2014; 63(10):3242-3252) For aging studies, male mice were maintained in group housing (3-4/cage) on standard rodent chow. Fasting glucose and glucose clearance were assessed in mice fasted for 6h.

Glucose tolerance tests were performed using 1 mg/kg dextrose administered intraperitoneally (ip.), as previously described. (Kumar, et al., (2008) Cell metabolism, 8, 468-481; Gao, et al., (2014) Diabetes 63, 3242-3252)

For visualization of cells expressing adropin, an IRES-Cre was inserted into the 3'untranslated region (UTR) of the adropin open reading frame in exon 2 (FIG. 1). The targeting vector was constructed using recombineering system. Isogenic DNA containing the Enho locus was retrieved from genomic colony RP23-100C7 of C57Bl/6 BAC genomic library via gap repair. An IRES-Cre-Frt-neo-Frt was inserted into 3' 53 bp downstream of the translational stop codon in exon 2. For gene targeting, 50 µg of linearized targeting vector consisting of 3.5 kb 5'arm and 7.2 kb 3' arm was electroporated into Bruce4 B6 embryonic stem (ES) cells. Correct homologous recombination in targeted clones was confirmed with Fidelity PCR at the 5' and 3' ends. The fragments produced from Fidelity PCR with these primers were sequenced to further verify the correctness of recombination. Correctly targeted ES cells were injected into Albino B6 blastocysts; germline transmitting chimeric mice were obtained and mated with Albino B6 mice to generate heterozygous carriers of the EnhoIRES-Cre-Frt-neo-Frt on the B6 background. The Frt-neo-Frt sequence was removed using B6; SJL-Tg(ACTFLPe)9205Dym/J transgenic mice purchased from the Jackson laboratory. EnhoIRES-Cre mice were then crossed onto the B6.Cg-Gt(ROSA)26Sortm9 (CAG-tdTomato)Hze/J strain in which a loxP-flanked stop cassette prevents transcription of a red fluorescent protein variant (tdTomato) driven by a CAG promotor (Madisen et al., (2010) Nature neuroscience.; 13(1):133-140).

Gene expression was assessed using qRT-PCR as previously described. Hippocampal and cortical tissue samples were dissected from fresh brains and snap frozen brains on dry-ice cold isopentane. Total RNA was extracted using Trizol (Invitrogen, Life Technologies) and treated with a DNAfree kit (Ambion, Life Technologies). 800 ng of total RNA were used for cDNA synthesis (Superscript III Reverse transcription kit, Invitrogen). Quantitative PCR was performed in 96-well plates using Taqman gene expression and QuantStudio 7 Detection Systems (Applied Biosystems, Life Technologies); 36B4 was used as the reference gene.

Assessment of Cognitive Function.

Memory retention and acquisition were assessed using an aversive T-maze and novel objective recognition, as previously described (Farr et al., (2016) J Alzheimers Dis.; 54(4):1339-1348). Briefly, the T-maze consists of a black plastic alley with a start box at one end and two goal boxes at the other. An electrifiable floor of stainless steel rods run throughout the maze to deliver a foot-shock using a scrambled grid floor shocker (Model E13-08, Coulbourn Instruments, Whitehall, PA). Mice are not permitted to explore the maze prior to training. A block of training trials begins when mice are placed in the start box. The guillotine door is raised and a cue buzzer sounded simultaneously (doorbell type, at 55 dB); 5s later a mild aversive foot-shock is applied with an intensity of 0.35 mA. The arm of the maze entered on the first trial is designated "incorrect" and the mild foot-shock continued until the mouse enters the other goal box, which in all subsequent trials is designated "correct" for each mouse. Mice are trained until they made one active avoidance, with an inter-trial interval of 30-35s. The number of trials to make one active avoidance is the measure of acquisition. Retention is tested 7d later, with training continued until the criterion of making five active avoidances in six consecutive trials is achieved. The number of trials needed to reach this criterion is the measure of retention(Butler et al., (2012) The Journal of clinical endocrinology and metabolism.; 97(10):3783-3791; Wong et al., (2014) The Journal of biological chemistry.; 289(37):25976-25986).

For the novel object recognition task, mice are habituated to an empty apparatus, a 58×66×11-cm white plastic box, for 5 min a day for 3 consecutive days prior to entry of objects. On the first day of training, mice are placed in the testing apparatus with two identical objects (A and B). 24h later the animal is reintroduced to the arena but this time one of the original objects is removed and a new object (C). Total time spent exploring each of the two objects is recorded. Anxiety will be assessed using open field and elevated plus maze tests. The experimental apparatus consists of a central platform, two open arms and two equal-sized closed arms opposite to each other. The test consisted of placing a mouse in the central platform facing an enclosed arm and allowing it to freely explore the maze for 5 min. The number of entries into the open and closed arms and the time spent in open arms was measure by an observer blind to treatment Statistical Analysis. Data were compiled in Microsoft Excel. Statistical analysis requiring analysis of covariance used univariate analysis in SPSS Statistics Version 23 (IBM). Student's t-test was used for comparisons of 2 groups.

Example 1

Figure 5:
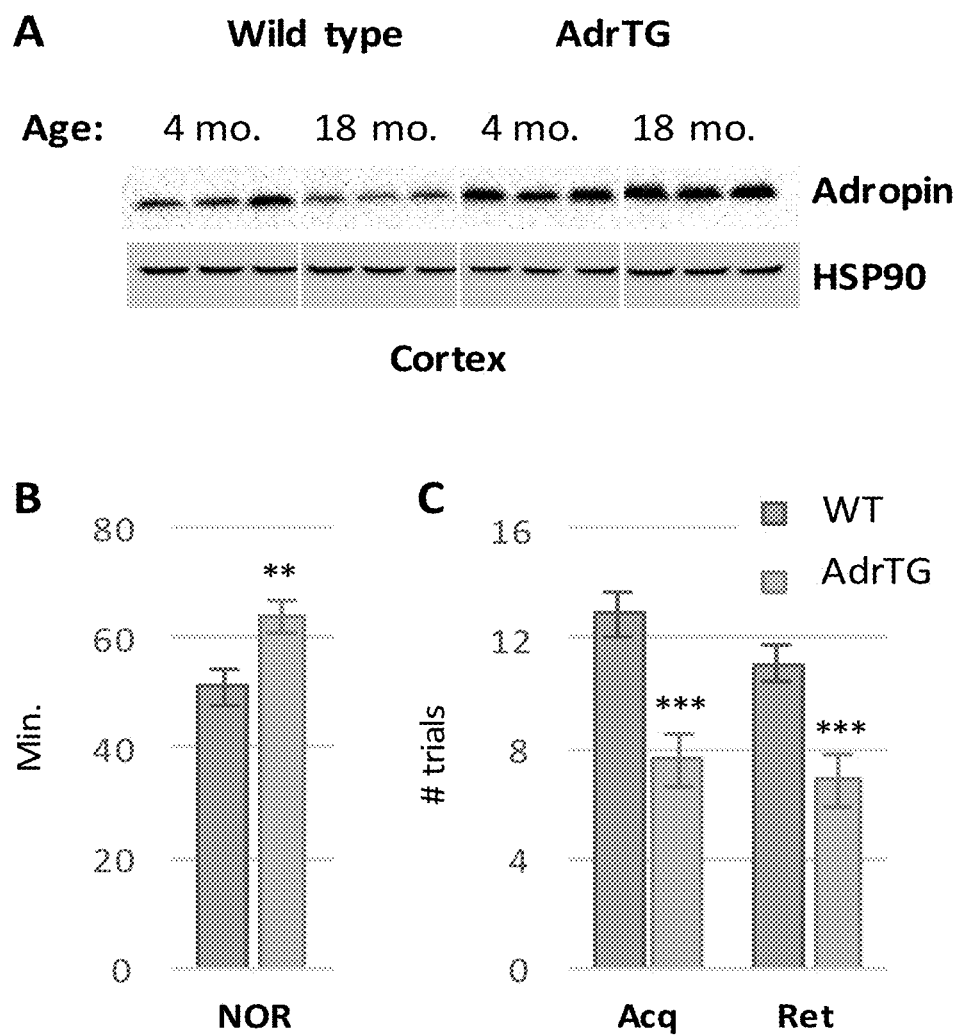
FIG. 5 Illustrates prevention of a decline in adropin protein in the nervous system with aging improves cognition in old B6 mice. (A) Western blot showing adropin protein in 4 and 18 month old AdrTG and age-matched wild type (WT) controls (n=3/group); HSP90 is presented as a loading control. (B-C) Learning and memory of male 18 mo. old AdrTG is significantly improved relative to aged matched WT controls (NOR: novel object recognition test; Acq: memory acquisition in aversive T-maze test; Ret: memory retention in aversive T-maze test) (AdrTG, n=11-14; WT, n=11-14). Significantly different from WT;  $p<0.01$; *, $p<0.001$ (Student's t-test).

The Inventors assessed cognitive performance using a strain of B6 mice over expressing the adropin open reading frame under the control of a human bβ-actin promotor (AdrTG) (Kumar, et al., (2008) Cell metabolism, 8, 468-481; Gao, et al., (2014) Diabetes 63, 3242-3252). Analysis of male adropin transgenic mice (AdrTG), mice aged <1 yr, suggested normal performance in tests of declarative memory, and of spatial learning and memory (data not shown). However, at 18 months of age, clear differences in performance were noted (FIG. 3), indicating a neuroprotective role from age related cognitive decline. Alternatively, there may be a "ceiling effect" in younger mice, with improved cognitive performance only observed when the ability for memory consolidation declines in the control group. Performance in tests of declarative memory, and of spatial learning and memory, were not significantly different in AdrTG and littermate controls aged <12 months (data not shown). However, at 18 months AdrTG exhibited significantly improved cognitive performance (FIG. 5). Adropin signaling in the CNS may thus prevent and/or delay cognitive decline observed with aging of male B6 mice. The transgenic animals created by the inventors demonstrate that if adropin levels in the brain are maintained, cognitive decline may be slowed, delayed or prevented.

Example 2

Figure 6:
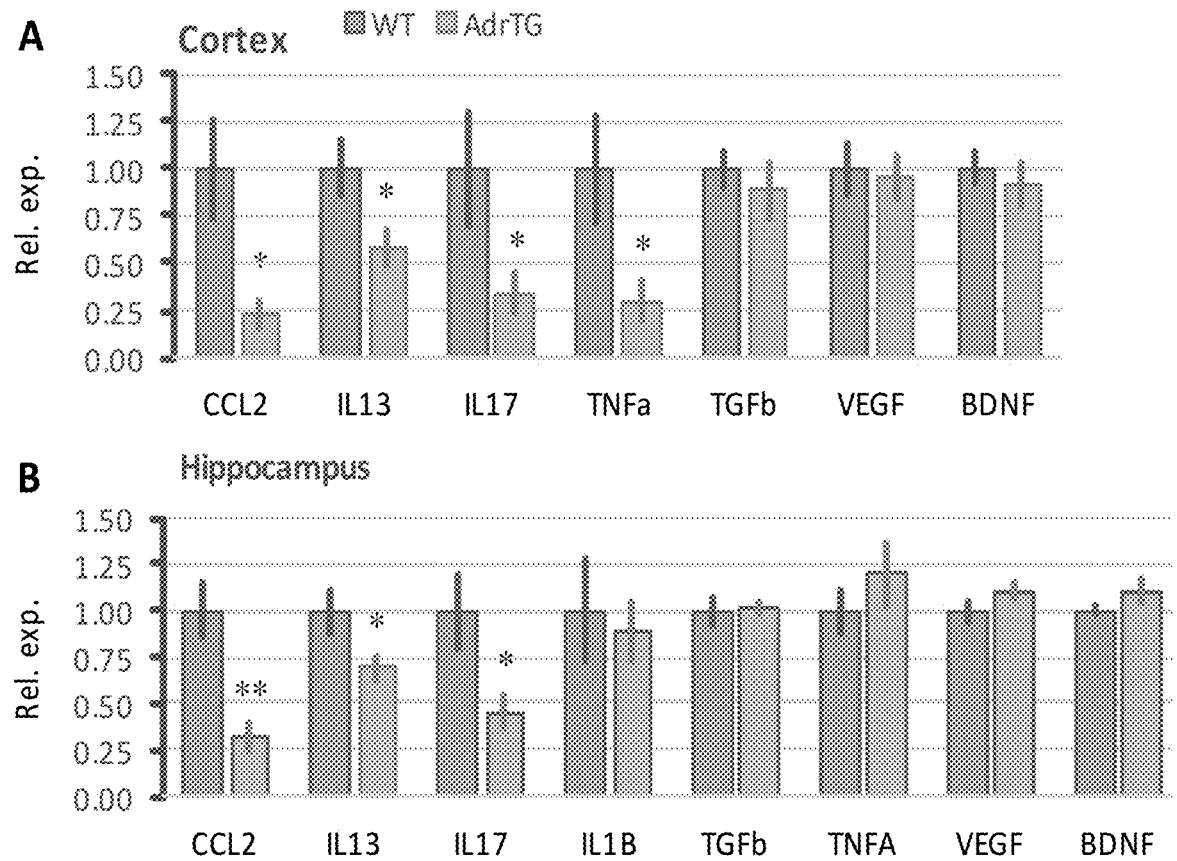
FIG. 6 illustrates reduced expression of inflammatory cytokines in cortical (A) and hippocampal (B) tissue samples from 18 mo. old AdrTG relative to age-matched controls. *, $p<0.05$; **, $p<0.01$.
Figure 7:
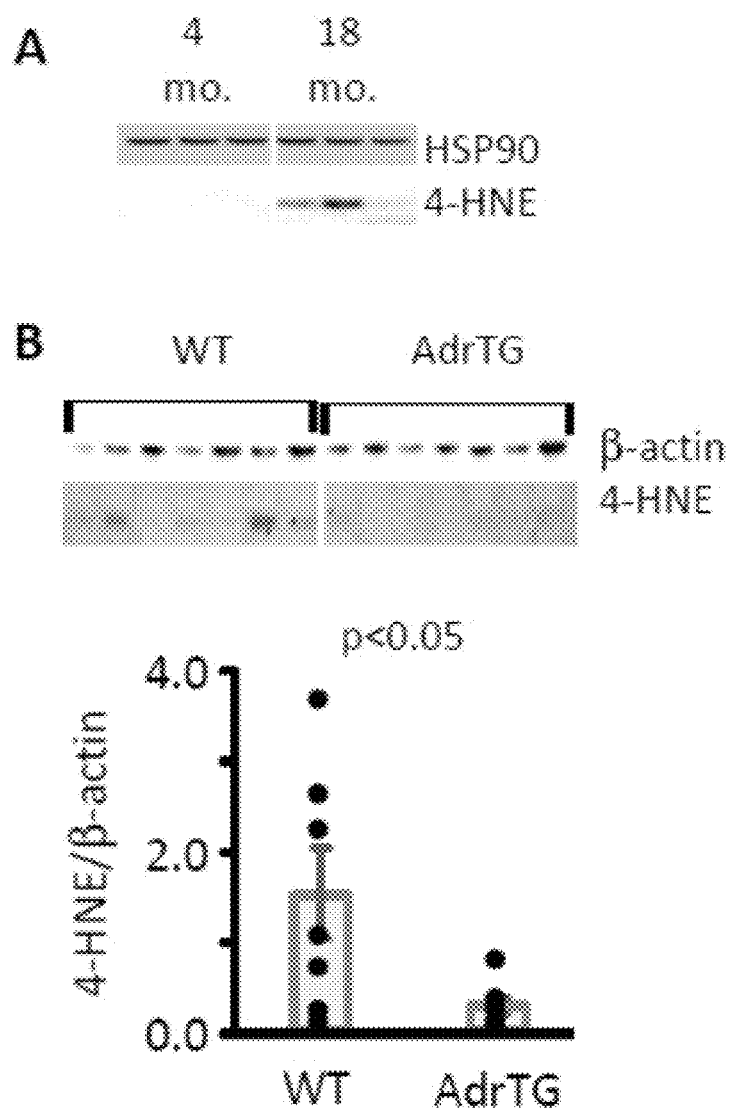
FIG. 7 illustrates Western blots indicating increased 4-HNE with aging in male B6 mice (A), that suggest lower 4-HNE in 18-month old adropin transgenic mice (AdrTG) compared to age-matched control mice (B). In panel B, the western blot and quantitated data are shown.
Figure 8:
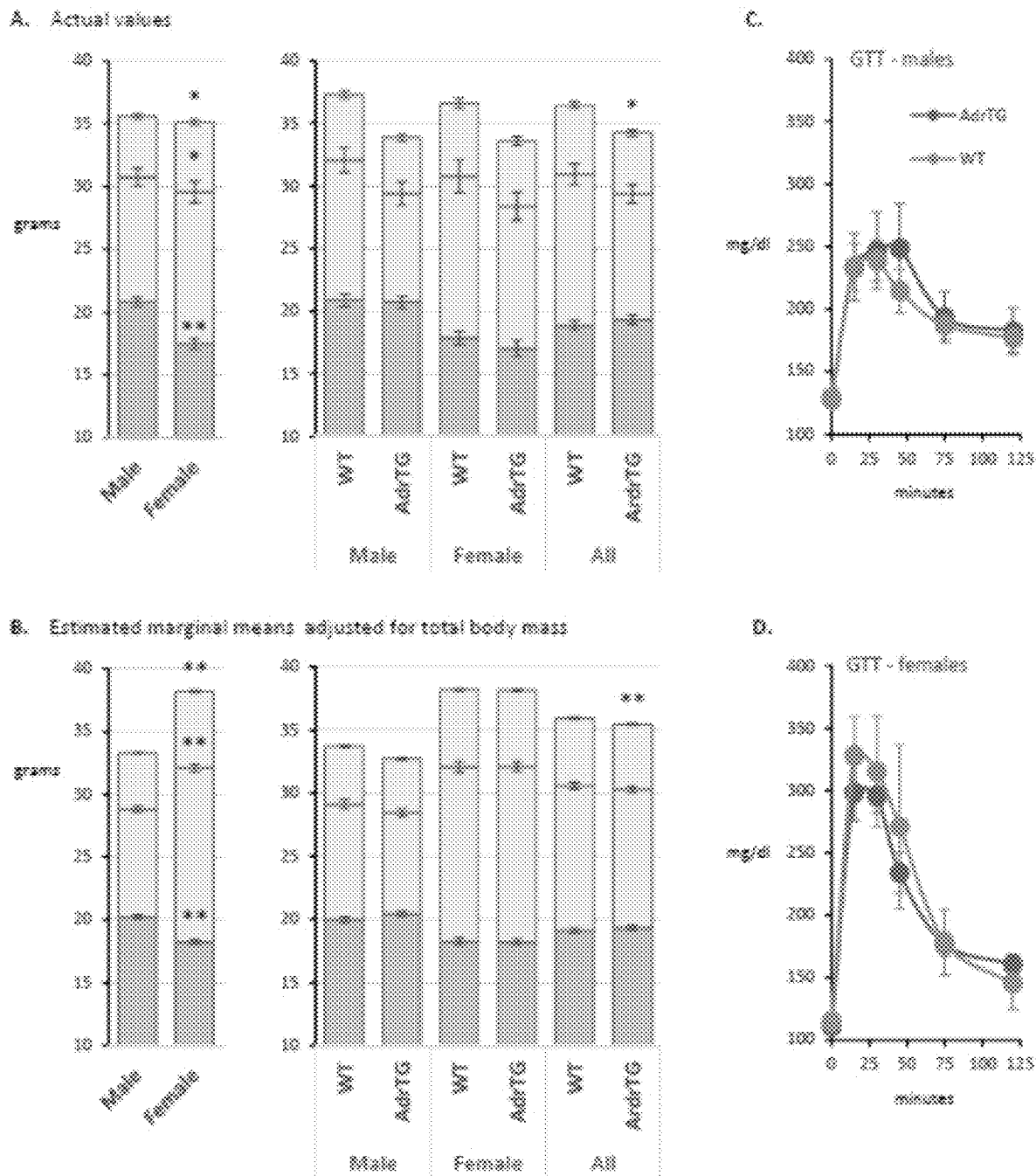
FIG. 8 Body composition (A-B) and glucose tolerance (C-D) are normal in 18 mo. old AdrTG mice compared to age-matched controls.
Figure 9:
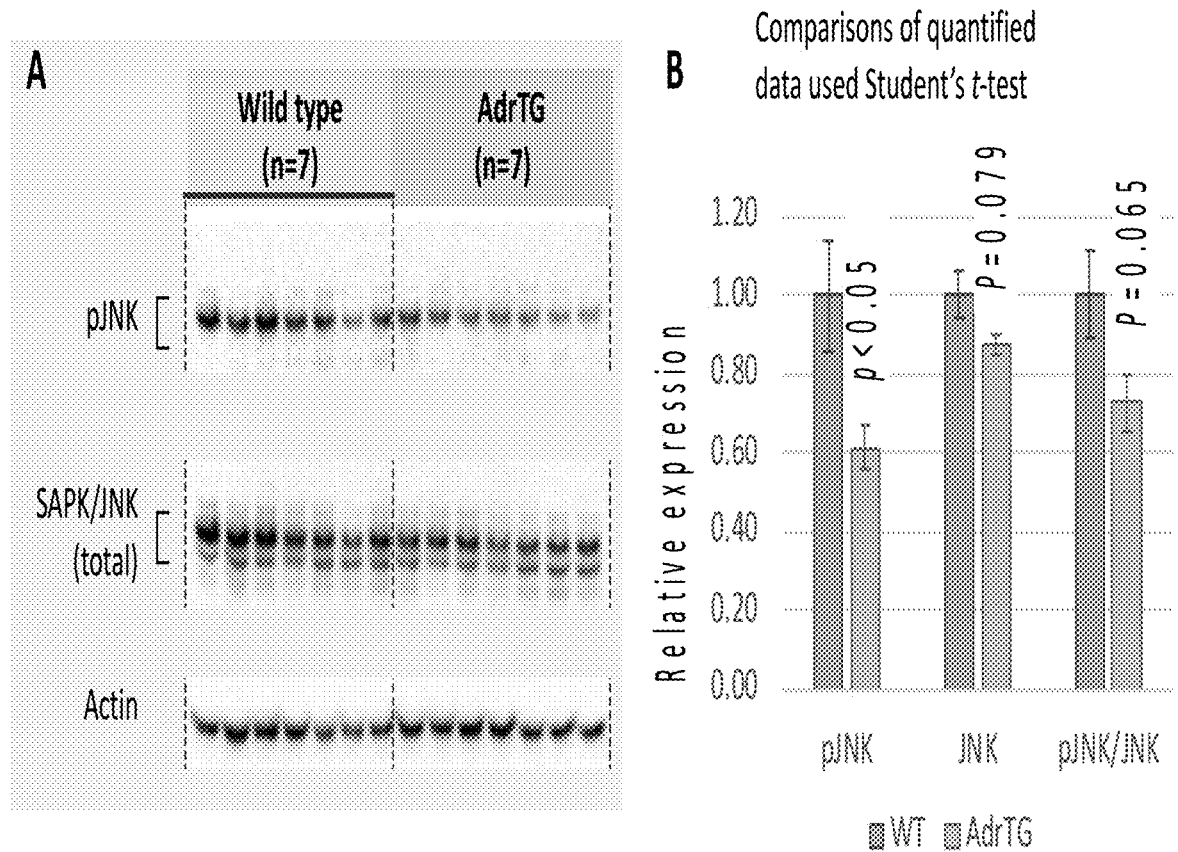
FIG. 9 illustrates reduced JNK phosphorylation (Thr183/Tyr185) in cortical extracts from 18-month old AdrTG mice compared to age-matched controls. Western blot showing phosphorylated JNK (pJNK), total JNK and Actin immunoreactivity (A). Quantitation of pJNK, total JNK (adjusted for actin) and the pJNK/JNK ratio (B).

Continuous exposure to adropin reduces stress in transgenic mice. Adropin transgenic mice show reduced stress indicators compared to wide type. Reduced inflammation (FIG. 6) and reduced oxidative stress (FIG. 7) are seen in AdrTG transgenic mice. Reduced expression of inflammatory cytokines in cortical (FIG. 6A) and hippocampal (FIG. 6B) are seen in tissue samples from 18 mo. old AdrTG relative to age-matched controls. *, $p<0.05$; **, $p<0.0$. In addition, increased 4-HNE is seen with aging in male B6 mice (FIG. 7A), but less so in adropin transgenic mice (AdrTG) (FIG. 7B) suggesting a relative reduction in oxidative stress in the AdrTG transgenic mice. Body composition (FIG. 8A-B) and glucose tolerance (FIG. 8C-D) are normal in 18 mo. old AdrTG mice compared to age-matched controls. Reduced SAPK/JNK activity in the nervous system of 18-month old adropin transgenic mice is consistent with reduced neuroinflammation (FIG. 9). The stress-activated protein kinase/Jun-amino-terminal kinase SAPK/JNK is potently and preferentially activated by a variety of environmental stresses including UV and gamma radiation, ceramides, inflammatory cytokines, and in some instances, growth factors and GPCR agonists (1-6). As with the other MAPKs, the core signaling unit is composed of a MAPKKK, typically MEKK1-MEKK4, or by one of the mixed lineage kinases (MLKs), which phosphorylate and activate MKK4/7. Upon activation, MKKs phosphorylate and activate the SAPK/JNK kinase (Ichijo, (1999) Oncogene 18, 6087-93.). Stress signals are delivered to this cascade by small GTPases of the Rho family (Rac, Rho, cdc42) (Kyriakis and Avruch, (2001) Physiol Rev 81, 807-69.). Both Rac1 and cdc42 mediate the stimulation of MEKKs and MLKs (Id.). Alternatively, MKK4/7 can be activated in a GTPase-independent mechanism via stimulation of a germinal center kinase (GCK) family member (Kyriakis (1999) J Biol Chem 274, 5259-62.). There are three SAPK/JNK genes each of which undergoes alternative splicing, resulting in numerous isoforms (Kyriakis and Avruch, (2001) Physiol Rev 81, 807-69.). SAPK/JNK, when active as a dimer, can translocate to the nucleus and regulate transcription through its effects on c-Jun, ATF-2, and other transcription factors (Kyriakis and Avruch, (2001) Physiol Rev 81, 807-69; Leppa and Bohmann (1999) Oncogene 18, 6158-62.).

Total JNK was measured by Western Blot using Recombinant Anti-JNK2 antibody [EP1595Y] (ab76125) from Abcam. Phosphorylation of JNK (an indicator of activation) was measured using Phospho-SAPK/JNK (Thr183/Tyr185) Antibody #9251 (Cell Signaling Technology). The Phospho-SAPK/JNK (Thr183/Tyr185) Antibody detects endogenous levels of p46 and p54 SAPK/JNK dually phosphorylated at threonine 183 (Thr183) and tyrosine 185 (Tyr185). Actin was detected using Cell Signaling 3700s (monoclonal antibody), and is used to estimate loading.

Example 3

To examine the effects of endogenous adropin on a subject's cognitive ability, 34 male C57BL/6J (B6) mice, aged 18 months, were treated with exogenous adropin[34-76]. Mice were purchased from The Jackson Laboratory (Bar Harbor, ME). After acclimation for 1 month, mice were separated into two weight matched groups of 15 mice: Group 1 adropin[34-76] treatment group and Group 2 saline vehicle control.

The mice were administered a single intraperitoneal injection (volume 100 μl) each morning (0900h) for 4 weeks. Group 1 was administered adropin[34-76] at a dose of 90 nmol/kg/day. Group 2 was administered saline. The peptide was purchased from Neoscientific Inc. Behavioral testing began after 2 weeks of injections. Injections continued though testing until 4 weeks.

Figure 10:
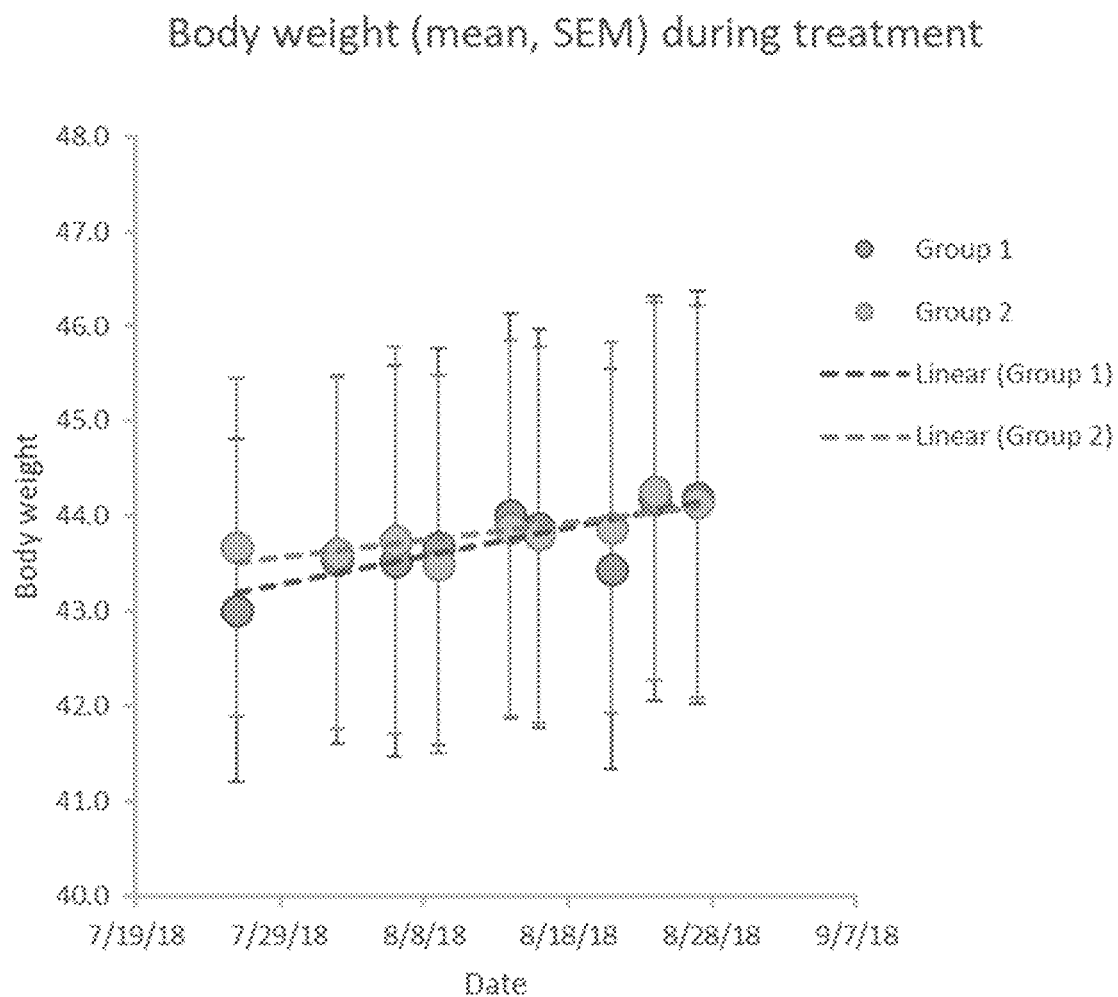
FIG. 10 illustrates body weight in 18-month-old male C57BL/6J (B6) mice treated with vehicle or exogenous adropin$^{34-76}$.

There was no significant effect of adropin[34-76] treatment on body weight (mean±SD for weight gain in grams for group 1, 0.7±3.1; group 2, 0.6±2.3, p=0.95 by Student's t-test). One mouse in group 1 died on 08/23/19. (FIG. 10)

Example 4

Figure 11:
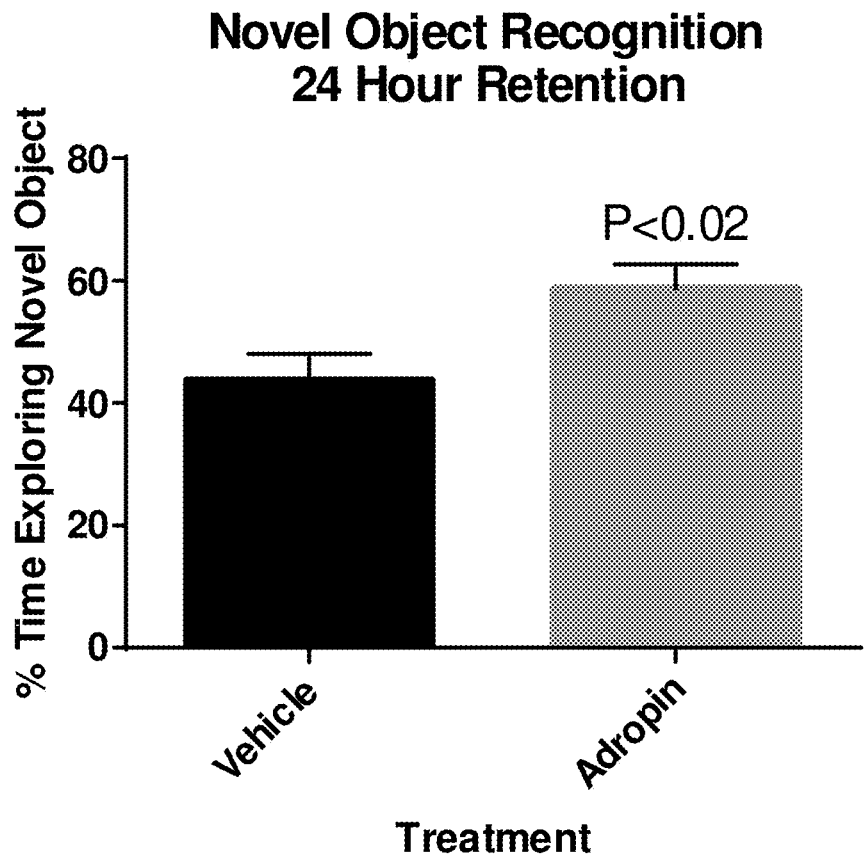
FIG. 11 illustrates Novel Object Recognition in 18-month-old male C57BL/6J (B6) mice treated with vehicle or exogenous adropin$^{34-76}$.

Adropin treatment improved cognitive performance as measured by the Novel Object Recognition test (FIG. 11, Table 1). A non-amnesic subject will spend more time exploring the novel object than the familiar one. When adropin treated and vehicle treated mice were subjected to the Novel Object Recognition test, adropin treated mice spent more time exploring the novel object (FIG. 11, Table 1)

TABLE 1

Novel Object Recognition test 24 Hour delay % Novel Object

| Vehicle | Adropin |
|---|---|
| 65.00 | 40.74 |
| 43.48 | 64.58 |
| 46.88 | 62.50 |
| 40.00 | 58.82 |
| 31.48 | 55.56 |
| 44.44 | 77.50 |
| 0.00 | 66.67 |
| 42.50 | 79.10 |
| 60.00 | 51.06 |
| 40.00 | 100.00 |
| 52.94 | 51.61 |
| 33.33 | 46.43 |
| 52.63 | 42.86 |
| 71.79 | 53.06 |
| 33.96 | 37.50 |

Statistical analysis of Table 1.

| Statistical analysis | Data 1 |
|---|---|
| Column B | Adropin |
| vs. | vs. |
| Column A | Vehicle |
| Unpaired t test | |
| P value | 0.0183 |
| P value summary | * |
| Significantly different? ($P < 0.05$) | Yes |
| One- or two-tailed P value? | Two-tailed |
| t, df | t = 2.505 df = 28 |
| How big is the difference? | |
| Mean ± SEM of column A | 43.90 ± 4.350, n = 15 |
| Mean ± SEM of column B | 58.88 ± 4.106, n = 15 |
| Difference between means | 14.99 ± 5.982 |
| 95% confidence interval | 2.733 to 27.24 |
| R squared | 0.1831 |
| F test to compare variances | |
| F, DFn, Dfd | 1.122, 14, 14 |
| P value | 0.8320 |
| P value summary | ns |
| Significantly different? ($P < 0.05$) | No |

Example 5

Figure 12:
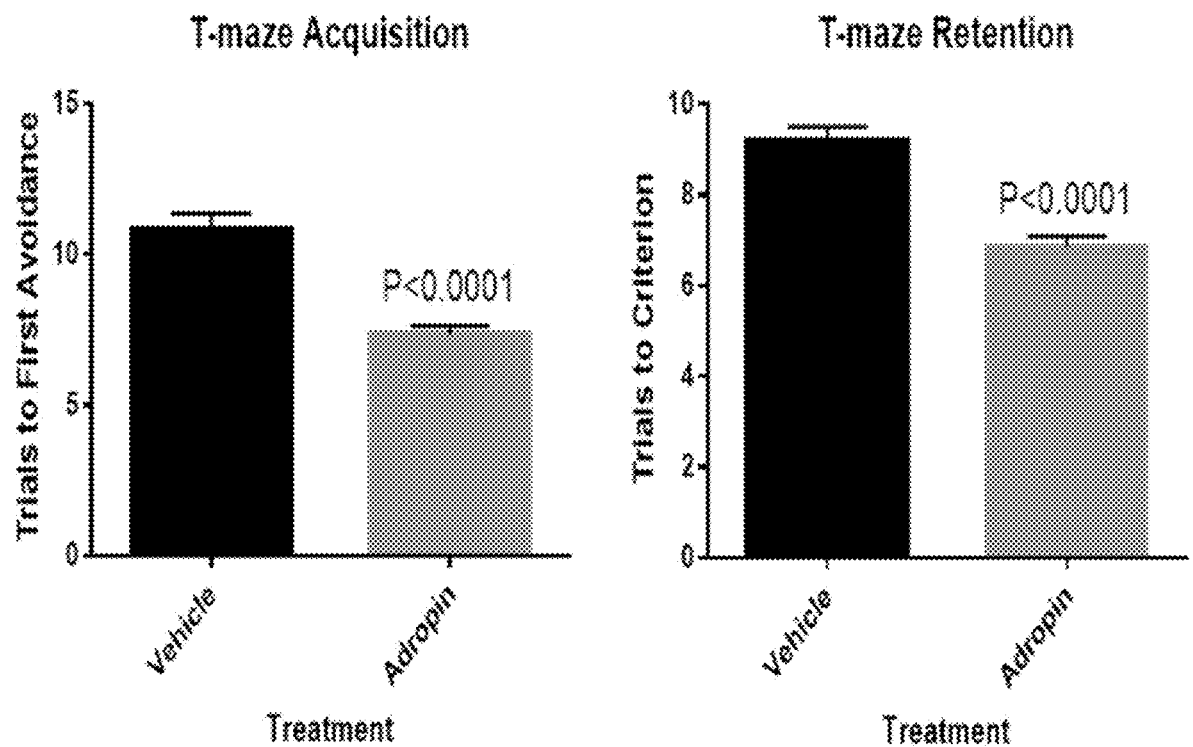
FIG. 12 illustrates T-maze Acquisition and T-maze Retention in 18-month-old male C57BL/6J (B6) mice treated with vehicle or exogenous adropin$^{34-76}$.

Adropin treatment also improved performance during the Acquisition T-maze test. Mice prepared with adropin or placebo in Example 3 were subjected to the Acquisition T-maze test. Adropin treated mice performed better (reduced time in maze) then placebo treated mice (FIG. 12, Table 2).

TABLE 2

T- maze acquisition

| Vehicle | Adropin |
|---|---|
| 8. | 7. |
| 13. | 6. |

TABLE 2-continued

| T- maze acquisition | |
| --- | --- |
| Vehicle | Adropin |
| 10. | 7. |
| 7. | 8. |
| 8. | 8. |
| 12. | 7. |
| 9. | 8. |
| 10. | 9. |
| 14. | 6. |
| 12. | 9. |
| 13. | 7. |
| 13. | 6. |
| 10. | 8. |
| 11. | 7. |
| 12. | |

| Statistical analysis of Table 2 | |
| --- | --- |
| Statistical analysis | T-maze Act |
| Column B | Adropin |
| vs. | vs. |
| Column A | Vehicle |
| Unpaired t test | |
| P value | <0.0001 |
| P value summary | **** |
| Significantly different? ($P < 0.05$) | Yes |
| One- or two-tailed P value? | Two-tailed |
| t, df | t = 5.464 df = 27 |
| How big is the difference? | |
| Mean ± SEM of column A | 10.80 ± 0.5538, n = 15 |
| Mean ± SEM of column B | 7.357 ± 0.2695, n = 14 |
| Difference between means | −3.443 ± 0.6301 |
| 95% confidence interval | −4.736 to −2.150 |
| R squared | 0.5251 |
| F test to compare variances | |
| F, DFn, Dfd | 4.525, 14, 13 |
| P value | 0.0099 |
| P value summary | ** |
| Significantly different? ($P < 0.05$) | Yes |

Adropin treated mice also showed superior performance in the T maize retention. (FIG. 12, Table 3) Mice were retested in the maze after 7 days and Adropin treated mice retained learned memories and complete the maze in lets time.

TABLE 3

| T-maze Retention | |
| --- | --- |
| Vehicle | Adropin |
| 9. | 6. |
| 9. | |
| 10. | 7. |
| 11. | 6. |
| 7. | 6. |
| 9. | 7. |
| 9. | 7. |
| 11. | 8. |
| 9. | 6. |
| 9. | 6. |
| 9. | 9. |
| 9. | 7. |
| 10. | 7. |

TABLE 3-continued

| T-maze Retention | |
| --- | --- |
| Vehicle | Adropin |
| 7. | 7. |
| 10. | 7. |

| Statically analysis of Table 3 | |
| --- | --- |
| Statically analysis | T-maze Ret |
| Column B | Adropin |
| vs. | vs. |
| Column A | Vehicle |
| Unpaired t test | |
| P value | <0.0001 |
| P value summary | **** |
| Significantly different? ($P < 0.05$) | Yes |
| One- or two-tailed P value? | Two-tailed |
| t, df | t = 6.178 df = 27 |
| How big is the difference? | |
| Mean ± SEM of column A | 9.200 ± 0.2960, n = 15 |
| Mean ± SEM of column B | 6.857 ± 0.2310, n = 14 |
| Difference between means | −2.343 ± 0.3792 |
| 95% confidence interval | −3.121 to −1.565 |
| R squared | 0.5857 |
| F test to compare variances | |
| F, DFn, Dfd | 1.759, 14, 13 |
| P value | 0.3169 |
| P value summary | ns |
| Significantly different? ($P < 0.05$) | No |

Example 6

Epidemiological studies suggest that the development of hypercholesterolemia in the mid- (as opposed to late-) stages of life associates with increased risk for Alzheimer's disease. Type 2 diabetes is also a major risk factor for dementia and is commonly associated with dyslipidemia. The inventors set out to demonstrate that adropin would be protective under such conditions and to this end, crossbreed transgenic mice to produce mice with severe metabolic dysregulation, which were also continuously exposed to elevated levels of adropin. Low-density lipoprotein receptor deficient (Ldlr−/−) mice were used as a model of hypercholesterolemia (see Ishibashi, et. al. J. Clin. Invest., 92 (1993), pp. 883-893). Adropin transgenic mice (AdrTG) were crossed onto the Ldlr−/− background (see Ghoshal et. al., Mol Metab. 2018 February; 8:51-64.). It was found that the adropin transgene did not prevent hypercholesterolemia due to loss of LDLR.

To further enhance the effects of metabolic dysregulation in their transgenic mouse model, the inventors placed these mice on a high fat/high sugar diet (HDF) (Research Diets 12451, 45% kcal/fat, 35% kcal/sucrose, 20% kcal/protein) for 3 months. At the end of this time, spatial learning and memory testing was compared between AdrTG; Ldlr−/− mice and Ldlr−/− mice. A group of 10 age-matched male C57BL/6J mice maintained on stand low-fat rodent chow were included as controls.

Figure 13:
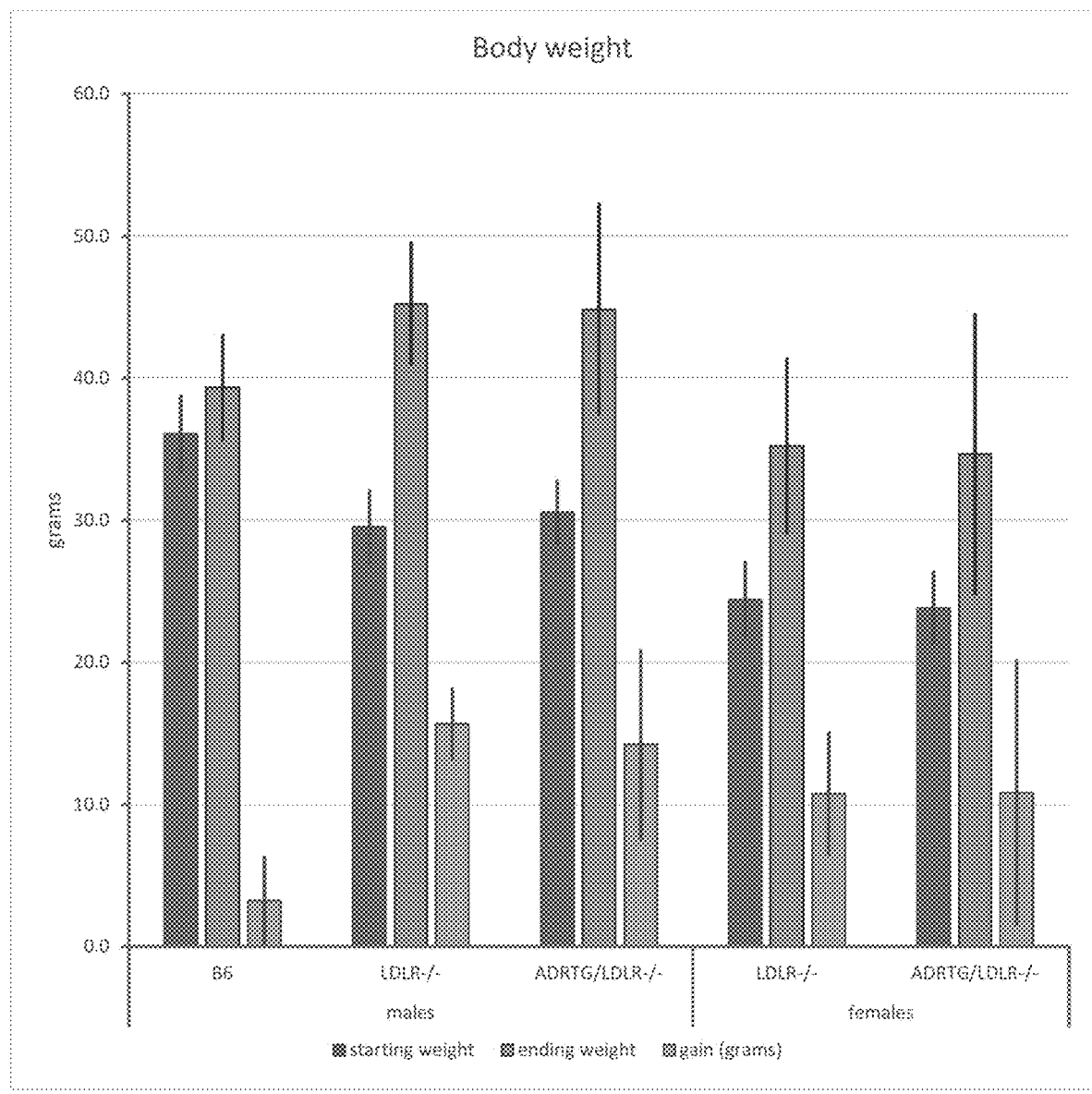
FIG. 13 illustrates body weight in C57BL/6J (B6), LdLr-/-, and ADRTG/LdLr-/-, male and female mice.
Figure 14:
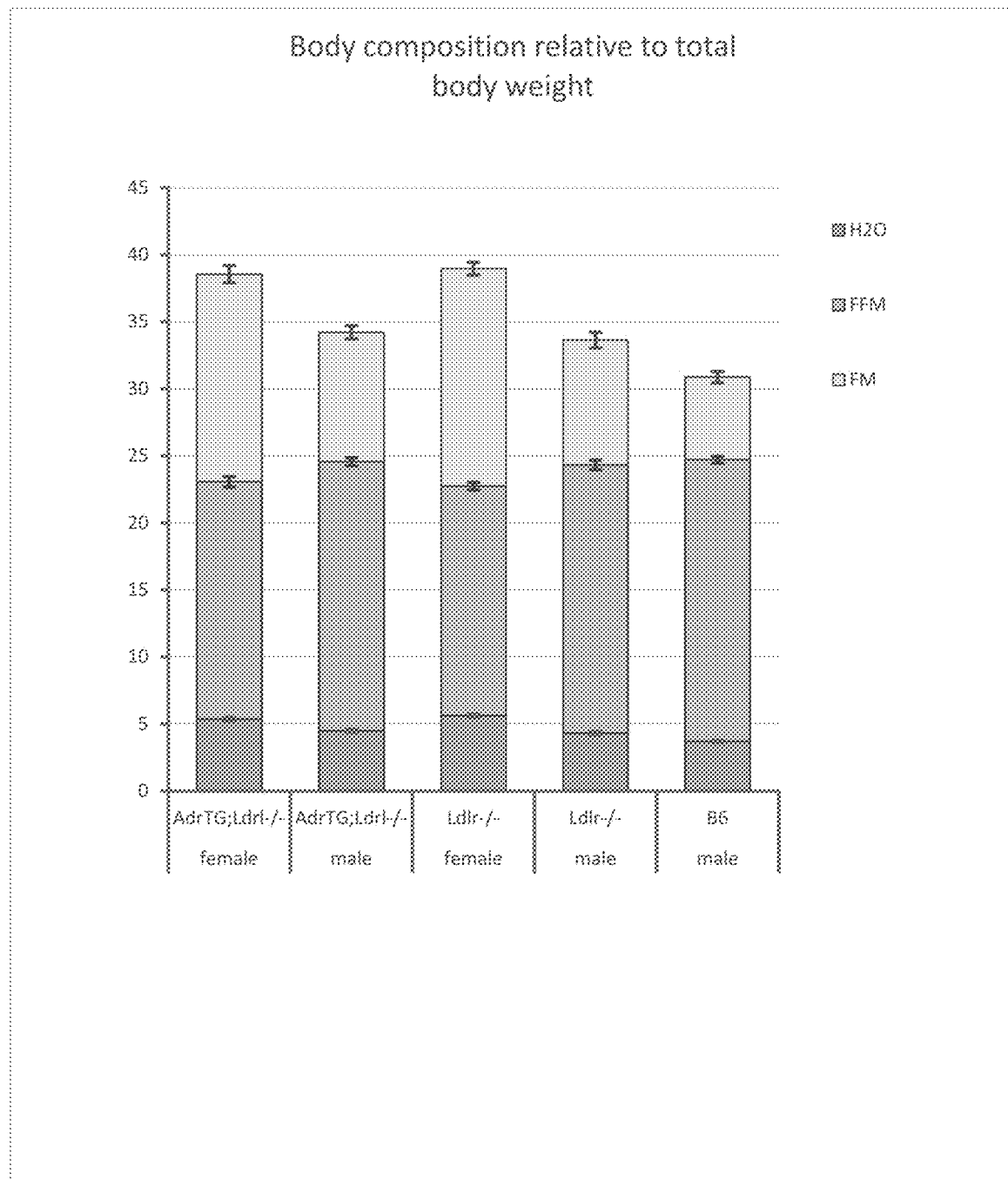
FIG. 14 illustrates body composition in C57BL/6J (B6), LdLr-/-, and ADRTG/LdLr-/-, male and female mice.

Ldlr−/− mice (11 females, 7 males), AdrTG; Ldlr−/− mice (6 females, 10 males) and age-matched C57BL/6J mice (n=12) were placed on a high fat diet for 3 months. Note all transgenic mice are on the same C57BL/6J background. Body composition was determined at baseline and after 3 months, after which cognitive function was assessed by Novel Object Recognition and Aversive T-maze testing. All mice gained weight during the study irrespective of sex (FIG. 13). Mice fed HFD gained more weight than B6 mice fed chow (13 grams vs. 3 grams). Body composition indicated increases in fat mass (FM) relative to total body weight in animals fed the HFD compared to the control group fed chow. (FIG. 14)

Fed blood glucose levels in all animals were high (>350 mg/dL), indicating dysregulation of glucose metabolism. (Table 4)

TABLE 4

Blood glucose levels in transgenic mice on HFC diets
Dependent Variable: Blood Glucose

| group | Mean | Std. Error | 95% Confidence Interval Lower Bound | 95% Confidence Interval Upper Bound |
|---|---|---|---|---|
| Female, Ldlr−/− | 400 | 24 | 353 | 448 |
| Male, Ldlr−/− | 443 | 29 | 384 | 501 |
| Female, AdrTG; Ldlr−/− | 374 | 29 | 315 | 432 |
| Male, AdrTG; Ldlr−/− | 462 | 25 | 411 | 513 |
| B6 chow | 356 | 21 | 313 | 399 |

Figure 15:
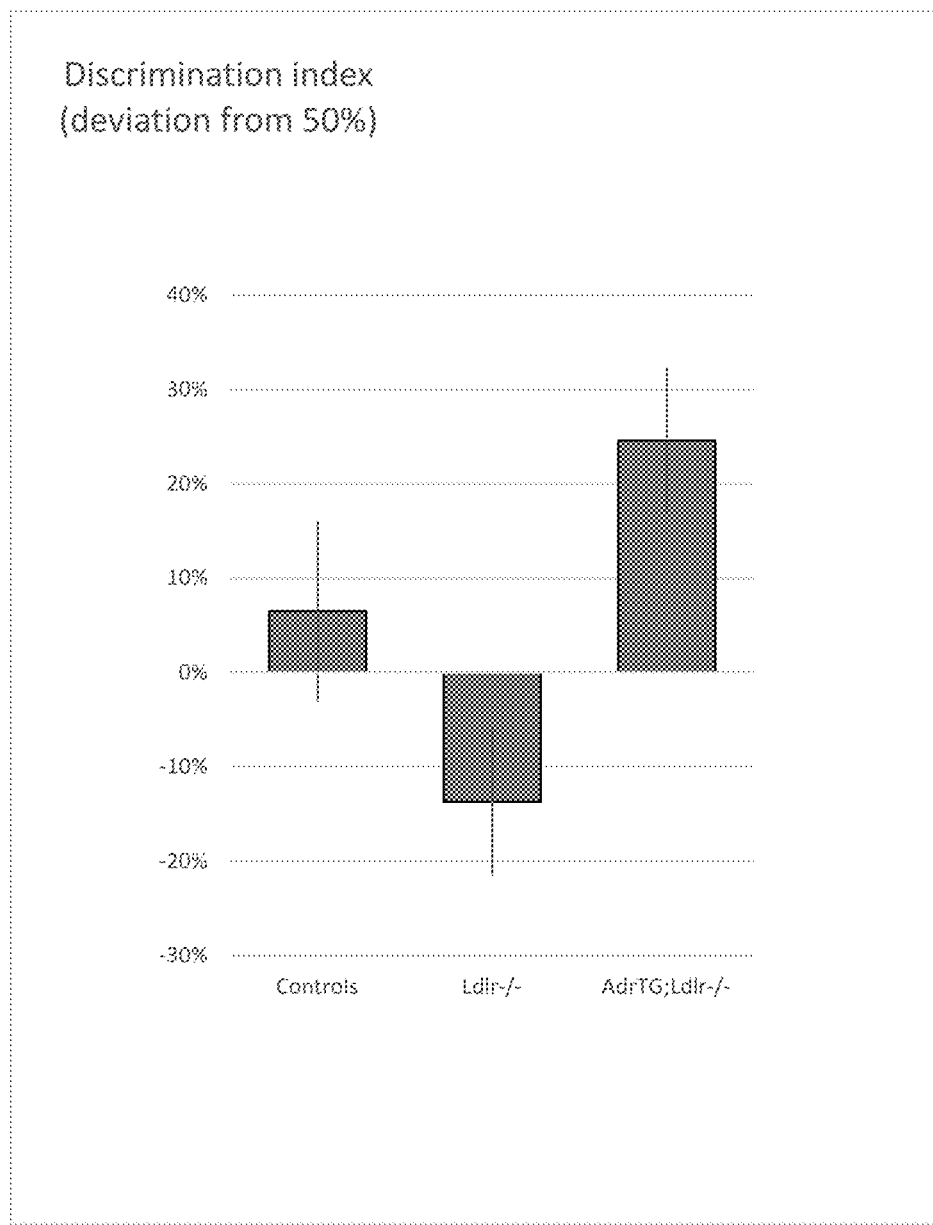
FIG. 15 illustrates Discrimination index, the percent of total time spent exploring with the novel object, in the Novel Object Recognition test. Controls (C57BL/6J (B6)), LdLr-/-, and ADRTG/LdLr-/-, transgenic mice.

Performance in the novel objective recognition (NOR) test was significantly improved in AdrTG; Ldlr−/− mice relative to Ldlr−/− mice, suggesting improved learning and memory. AdrTG; Ldlr−/− mice spent significantly more time exploring the novel object compared to Ldlr−/− mice. Values are adjusted for sex (FIG. 15).

The inventors demonstrated that the adropin transgene improves cognitive function in a mouse model of type 2 diabetes and hypercholesterolemia. Older patients with type 2 diabetes who are at increased risk for dementia, and who may exhibit symptoms of mild cognitive impairment, could therefore benefit from treatment with adropin[34-76] administered by daily injection or any of the treatment methods discussed herein.

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating a subject in need thereof medically diagnosed with age-related cognitive decline and a decreased level of adropin compared to a previous level of adropin in the subject, the method comprising administering to the subject an effective amount of the adropin amino acid sequence of SEQ ID NO: 1 or the adropin34-76 peptide fragment amino acid sequence of SEQ ID NO: 2, wherein the effective amount is sufficient to delay or not allow further progression of age-related cognitive decline as determined by a medically diagnosing professional on a subject by subject basis as to the subject in need thereof; by measuring the before and after treatment results of any standard cognitive functioning test that specifically tests for age-related cognitive decline.

2. The method of claim 1, wherein the effective amount is 1000 nmol/kg/day to 1 nmol/kg/day.

3. The method of claim 1, wherein an effective amount is 450 nmol/kg/day.

4. The method of claim 1, wherein the effective amount is 90 nmol/kg/day.

5. The method of claim 1, wherein the effective amount is administered daily.

6. The method of claim 1, wherein the effective amount is administered one or more times a day, over a period of 2 or more weeks.

7. The method of claim 1, wherein administering is by parenteral injection by a parenteral route selected from the group consisting of intraperitoneal, subcutaneous, intramuscular, and intravenous.

8. The method of claim 1, wherein administering an effective amount the adropin amino acid sequence of SEQ ID NO: 1 or the adropin34-76 peptide fragment amino acid sequence of SEQ ID NO: 2 consists of administering an oligonucleotide that expresses the adropin amino acid sequence of SEQ ID NO: 1 or the adropin34-76 peptide fragment amino acid sequence of SEQ 1D NO: 2.

9. The method of claim 1, wherein the subject is a human subject.

10. The method of claim 1, wherein the subject diagnosed with mild cognitive impairment presents a family history of, or has also been diagnosed with, type 2 diabetes.

11. The method of claim 1, wherein the subject diagnosed with mild cognitive impairment presents a family history of, or has also been diagnosed with, a gene for hypercholesterolemia.

* * * * *

SEQUENCE LISTING

```
<160> NUMBER OF SEQ ID NOS: 2

<210> SEQ ID NO 1
<211> LENGTH: 76
<212> TYPE: PRT
<213> ORGANISM: Homo sapiens

<400> SEQUENCE: 1

Met Gly Ala Ala Ile Ser Gln Gly Ala Leu Ile Ala Ile Val Cys Asn
1               5                   10                  15

Gly Leu Val Gly Phe Leu Leu Leu Leu Trp Val Ile Leu Cys Trp
            20                  25                  30

Ala Cys His Ser Arg Ser Ala Asp Val Asp Ser Leu Ser Glu Ser Ser
            35                  40                  45

Pro Asn Ser Ser Pro Gly Pro Cys Pro Glu Lys Ala Pro Pro Pro Gln
    50                  55                  60

Lys Pro Ser His Glu Gly Ser Tyr Leu Leu Gln Pro
65                  70                  75

<210> SEQ ID NO 2
<211> LENGTH: 43
<212> TYPE: PRT
<213> ORGANISM: Homo sapiens

<400> SEQUENCE: 2

Cys His Ser Arg Ser Ala Asp Val Asp Ser Leu Ser Glu Ser Ser Pro
1               5                   10                  15

Asn Ser Ser Pro Gly Pro Cys Pro Glu Lys Ala Pro Pro Pro Gln Lys
            20                  25                  30

Pro Ser His Glu Gly Ser Tyr Leu Leu Gln Pro
            35                  40
```